(12) United States Patent
Chiang

(10) Patent No.: US 6,472,216 B1
(45) Date of Patent: Oct. 29, 2002

(54) AQUEOUS TISSUE CLEARING SOLUTION

(76) Inventor: Ann-Shyn Chiang, No. 101, Sec. 2, Guangfu Rd., Hsinchu (TW)

( * ) Notice: Subject to any disclaimer, the term of this patent is extended or adjusted under 35 U.S.C. 154(b) by 0 days.

(21) Appl. No.: 09/910,764

(22) Filed: Jul. 24, 2001

(51) Int. Cl.$^7$ .............................................. G01N 31/00
(52) U.S. Cl. ........................... 436/17; 436/8; 436/164; 436/166; 436/174; 435/40.5; 435/40.51; 435/40.52; 252/408.1
(58) Field of Search ............................... 436/8, 17, 164, 436/166, 174, 175; 252/408.1; 435/40.5, 40.51, 40.52

(56) References Cited

U.S. PATENT DOCUMENTS

| | | | | | |
|---|---|---|---|---|---|
| 5,318,795 A | * | 6/1994 | Stokes et al. | .................. | 427/4 |
| 5,344,637 A | * | 9/1994 | Camiener | ...................... | 435/4 |
| 5,514,379 A | * | 5/1996 | Weissleder et al. | .......... | 424/426 |
| 5,907,082 A | * | 5/1999 | O'Neill et al. | .............. | 536/23.6 |
| 6,042,874 A | * | 3/2000 | Visinoni et al. | ............ | 427/2.11 |
| 6,159,445 A | * | 12/2000 | Klaveness et al. | ............ | 424/9.1 |
| 6,165,798 A | * | 12/2000 | Brooks | ........................ | 436/169 |
| 6,219,575 B1 | * | 4/2001 | Nemati | ........................ | 128/898 |
| 6,232,092 B1 | * | 5/2001 | Rogers | ........................ | 435/40.5 |

* cited by examiner

Primary Examiner—Maureen M. Wallenhorst
(74) Attorney, Agent, or Firm—Rosenberg, Klein & Lee

(57) ABSTRACT

An aqueous tissue clearing solution for use in making biological tissues transparent is provided. The aqueous tissue clearing solution is selected from the group consisting of dimethyl sulfoxide, diatrizoate acid, ethylenediaminetetraacetic acid, glucamine, β-nicotinamide adenine dinucleotide phosphate, sodium diatrizoate, and derivatives of polyoxyalkalene. The aqueous tissue clearing solution is used to make tissue transparent for viewing through microscopy.

8 Claims, 3 Drawing Sheets

(3 of 3 Drawing Sheet(s) Filed in Color)

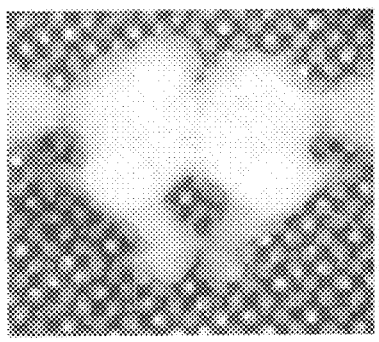 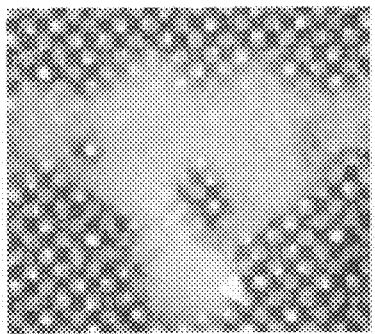 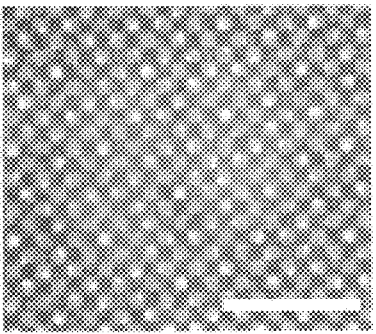
Fig.1A  Fig.1B  Fig.1C
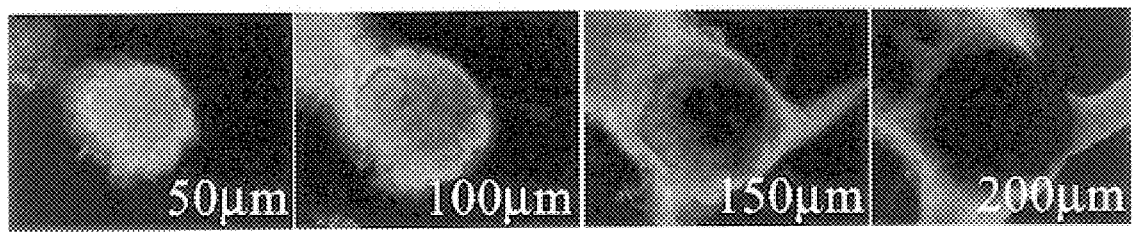
Fig.2A
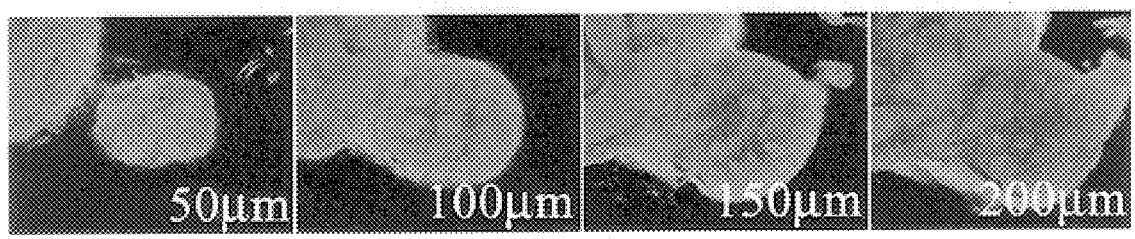
Fig.2B

AQUEOUS TISSUE CLEARING SOLUTION

FIELD OF THE INVENTION

The invention relates to a solution used in analysis of biological tissues and, more particularly, to the composition of an aqueous clearing solution making biological tissues transparent.

BACKGROUND OF THE INVENTION

For some lift sciences such as cell biology, neurobiology, molecular biology, physiology, immunology, signal biology, and development biology, to examine biological or non-biological planar or three-dimensional microscopic structures, in addition to having a good microscope such as a confocal microscope to obtain high-resolution images, it is also necessary to specially take care of preparation of samples, recording of microscopic images, and processing of images so that optics can be exploited to examine some samples and biological cells or tissues capable of emitting fluorescence. When preparing samples, it is necessary to assure the wholeness of three-dimensional structures of the samples in the processing procedure such as the fixation or mounting procedure.

Generally speaking, conventional transmitted light microscopy is extensively used in almost every biological laboratory for observation of cellular structures. Biological tissues are usually stained with dyes before they can be examined with microscopy. To view the stained internal structures, tissues are usually sectioned into thin slices. In order to increase tissue transparency, most preparations of stained samples are cleared by dehydration and lipid extraction processes. For example, xylene is often used to clear paraffin sections after alcohol dehydration. As a result, the stained internal features can be sharply focused.

However, solvent extraction requires more processing time and often causes morphology distortion and needs to be avoided in some situations. For example, cryosectionings performed for rapid diagnosis purpose are usually not fixed well. These tissue slices are usually embedded directly in glycerol-based aqueous mountant without clearing process to avoid destruction of the fragile morphology. The resulting microscopic images are thus suffered from decrease of clarity. Moreover, during the processes of examination, scanning, and image reconstruction of biological tissues, the reconstructed thickness can only reach 100~200 micrometers due to not good transparency of tissue samples.

Accordingly, the present invention proposes an aqueous clearing solution to effectively make biological tissues transparent without damaging tissues and without dehydration process. FIGS. 1A to 1C demonstrate that an insect brain of about 500 $\mu$m thick that is normally opaque in saline (FIG. 1A), semi-opaque in 80% glycerol-saline mixture (FIG. 1B) and completely transparent in the invented clearing solution (FIG. 1C).

SUMMARY OF THE INVENTION

The primary object of the present invention is to provide an aqueous tissue clearing solution making biological tissues transparent without dehydration process.

Another object of the present invention is to provide a method to process biological tissue processed by an aqueous tissue clearing solution to obtain images of higher resolution in fluorescent and non-fluorescent light microscopes.

Yet another object of the present invention is to provide an aqueous tissue clearing solution to make tissues transparent without damaging slices and detailed morphology of tissues.

To achieve the above objects, an aqueous tissue clearing solution of the present invention comprises one or more of dimethyl sulfoxide, diatrizoate acid, ethylenediaminetetraacetic acid, glucamine, β-nicotinamide adenine dinucleotide phosphate, sodium diatrizoate, and derivative of polyoxyalkalene (with a trade name of Tween 20 and used as emulsifying agent and detergent) in a suitable aqueous solution. This aqueous tissue clearing solution is utilized to make tissues transparent.

BRIEF DESCRIPTION OF THE DRAWINGS

The file of this Patent contains at least one drawing executed in color. Copies of the Patent with color drawings will be provided by the Patent and Trademark Office upon request and payment of the necessary fee.

FIGS. 1A to 1C show evaluation of tissue transparency. Brain tissues of about 500 $\mu$m thick are derived from the cockroach, *Diploptera punctata*, adult females. (A) The brain is opaque when incubated in the cockroach physiological saline solution. (B) The brain is semi-transparent in saline solution containing 80% glycerol. (C) The brain becomes completely transparent in the invented aqueous clearing solution.

FIGS. 2A and 2B show effects of tissue transparency on confocal imaging. Confocal image series of antennal glomeruli of the cockroach, *D. punctata* are taken at every 50$\mu$m Z-intervals. (A) The internal glomeruli become invisible at depth of 100 $\mu$m beneath the surface of the tissue when embedded in saline solution containing 80% glycerol. (B) The image of glomeruli remains clear even at 200 $\mu$m depth when embedded in the invented aqueous clearing solution.

DETAILED DESCRIPTION OF THE PREFERRED EMBODIMENTS

Figure 3:
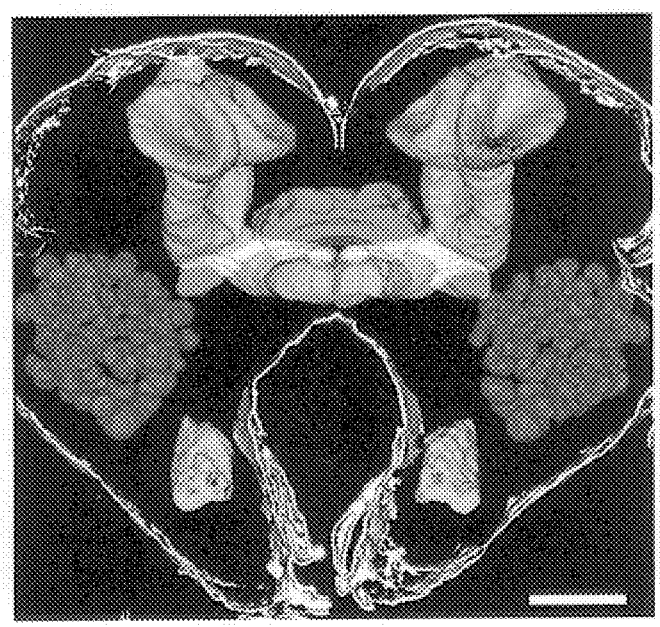
FIG. 3 shows a three-dimensional map of brain neuropils of the cockroach, *Diploptera punctata* adult female.

The present invention relates to an aqueous tissue clearing solution for use in making excised tissues transparent. The aqueous tissue clearing solution of the present invention comprises one or more of dimethyl sulfoxide, diatrizoate acid, ethylenediaminetetraacetic acid, glucamine, β-nicotinamide adenine dinucleotide phosphate, sodium diatrizoate, and derivative of polyoxyalkalene (with a trade name of Tween 20 and used as emulsifying agent and detergent) in a suitable aqueous solution. The pH value of the above solution is adjusted to the range of 5–10.

The above tissues comprise biological structures such as animal and plant cells, biological organisms, and biological compounds and devices.

Transparency can be achieved by direct incubation of the tissue in the invented clearing solution with or without prior fixation. A biological tissue having a better transparency is obtained after an incubation period. When a specific internal structure of interest is labeled with immunofluorescence or classical dyes, making transparency of components above and bellow the labeled object results in better imaging and higher detection sensitivity of the stained structure. Thus, making transparency with the invented aqueous clearing solution will enhance the observation and signal detection of fluorescent and non-fluorescent cellular structures during the application of optical detection methods such as confocal microscopy, fluorescence microscopy, conventional transmitted light microscopy, dissecting microscopy, flow cytometry, spectrophotometry, fluorescence plate detection and fluorescence chip detection, etc. The transparency achieved by using the aqueous tissue clearing solution of the present invention can enhance observation capability and signal detection sensitivity of fluorescent and non-fluorescent cellular structures.

Confocal microscopy offers the possibility of removing out-of-focus background fluorescence in a fluorescently labeled thick specimen and recording the X, Y and Z coordinates of objects that then can be rendered and analyzed three-dimensionally. Opacity of biological tissues thicker than 100 $\mu$m, about 5–10 cells thickness, normally prevents efficient excitation and sufficient signal strength for fluorescence detection. On the other hand, routine methods using serial alcohol dehydration and methyl salicylate-permeated clearing often result in diffusion of the labeled fluorochromes. Clearing and embedding the fluorochrome-labeled tissues in the invented clearing solution largely overcome these problems. For example, when embedded in 80% glycerol-saline mixture, the glomeruli within an insect's antennal lobe can only be confocally viewed up to 100 $\mu$m below the surface (FIG. 2A). In contrast, the internal structures deeper than 200 $\mu$m can still be clearly viewed when the sample is cleared and embedded in the invented aqueous clearing solution (FIG. 2B). Furthermore, the fluorescence NBD-ceramide, the membrane probe used for staining all lipophilic structures within biological tissues, will be gradually dissolved in glycerol-saline mixture. As a result, details of the labeled fine structures are no longer visible. In contrast, those details remain clear when the same tissue is embedded in the invented aqueous clearing solution.

The present invention will be illustrated by describing the following examples.

EXAMPLE 1
Microscopic Imaging of Thick Tissues Labeled with Fluorescent Probes An insect brain, more than 500 $\mu$m thick, of the cockroach *Diploptera punctata* is used for the demonstration. Neuropil structures and neuronal somata within the brain were stained with the lipophilic membrane probe NBD $C_6$-ceramide and DNA-probe propidium iodide. After proper fixation in 4% paraformaldehyde, nuclei within the brains were digested with 50$\mu$g/ml RNase and stained with 20$\mu$g/ml propidium iodide in phosphate buffered saline. Subsequently, after briefly rinsed in phosphate buffered saline, membranes were stained with 0.435 mM NBD $C_6$-ceramide in DMSO. The brain was making transparent by direct incubation in the invented clearing solution for one hour. To avoid compression under the coverslip, specimen were placed within spacer rings approximately 600$\mu$m in height and then subjected for confocal microscope imaging. The fluorescent structures within the entire brain can then be directly observed under a conventional fluorescence microscope or imaged with a confocal microscope. FIG. 3 shows a three-dimensional cockroach brain containing all internal neuropils reconstructed from computer-segmented images of 168 confocal optical slices. This would not be possible if the brain tissue is not transparent enough for laser penetration and fluorescence detection.

In addition to making whole-mount tissue transparent, the invented clearing solution can be also applied for tissue slices such as cryosections and vibratome slices.

Figure 4:
FIG. 4 shows a microscopic image of the mushroom bodies in a transparent cricket brain observed under a general transmitted light microscope.

EXAMPLE 2
Microscopic Imaging of Thick Tissues Labeled with Non-fluorescent Dyes The brain of the cricket, *Acheta domesticus,* is used for the demonstration. The brain was fixed in 4% paraformaldehyde in phosphate buffered saline (360 mOsM per Kg $H_2O$, pH 7.4) on ice for 2 hours. They were then washed 3 times in ice-cold PBS, 10 min each wash. The tissues were permeabilized by incubating them for 16 h at 4° C. in phosphate buffered saline containing 1% Triton X-100. After being washed with phosphate buffered saline, fixation-insensitive NADPH-diaphorase activity was visualized by incubating the tissues at 27° C. for 2 hours in 100$\mu$l Tris-HCl (50 mM, pH 7.4) containing 1% Triton X-100, 1 mM $\beta$-NADPH and 0.5 mM NBT. Blue formazan precipitates out of the solution and, in so doing, indicates sites where NADPH-diaphorase has reacted. Non-specific background precipitation was removed by extensive washing of tissues for 72 hours in Tris-HCl buffer containing 1% Triton X-100. After cleaning the surrounding connective tissues, the entire brain of more than 600$\mu$m thick was making transparent by direct incubation in the invented aqueous clearing solution for one hour. To avoid compression under the coverslip, specimen were placed within spacer rings mounted in the same aqueous clearing solution, viewed and photographed the tissue under a dissecting microscopy or with a Zeiss Axiophot (Carl Zeiss, Jena, Germany) compound microscope using Nomarski optics. FIG. 4 shows that high NADPH-diaphorase activity indicated with formazan precipitates occurred at the mushroom bodies. The internal mushroom bodies can be clearly viewed because the brain is made transparent by incubation in the invented clearing solution.

This method can be also applied for viewing structures within tissues slices derived from cryosections and vibratome slices labeled with non-fluorescent dyes.

Figure 5:
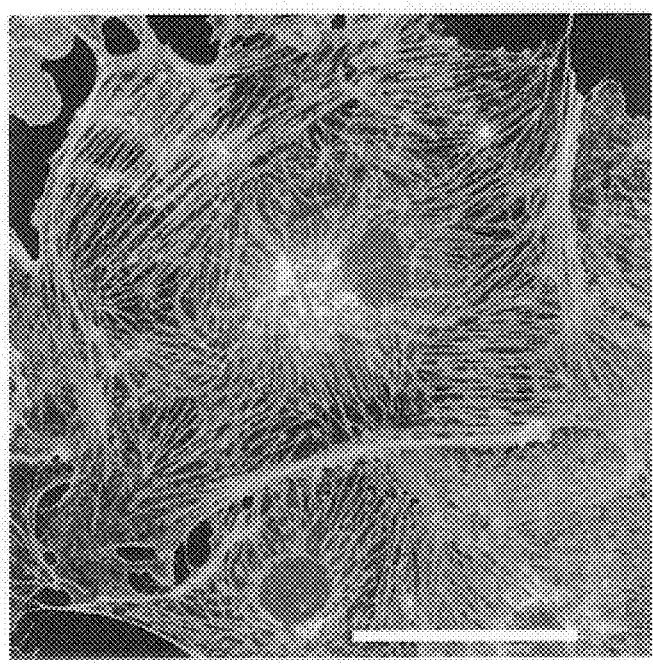
FIG. 5 shows a high-resolution confocal image of human fibroblasts embedded in the invented aqueous clearing solution.

EXAMPLE 3
Microscopic Imaging of Single Cells Labeled with Fluorescent or Non-fluorescent Probes Fixed single cells on the slides can be directly cleared and mounted in the invented clearing solution. The aqueous nature of the clearing solution allows its direct usage for immunofluorescence- or other fluorochrome-labeled single cells. FIG. 5 shows that high degree of transparency largely improves the resolution and sensitivity for image detection using confocal microscope. Because of the improved transparency, excitation efficiency and emission detection sensitivity are greatly increased. Therefore, application of smaller pinhole for removing out-of-focus background fluorescence can be applied.

Figure 6:
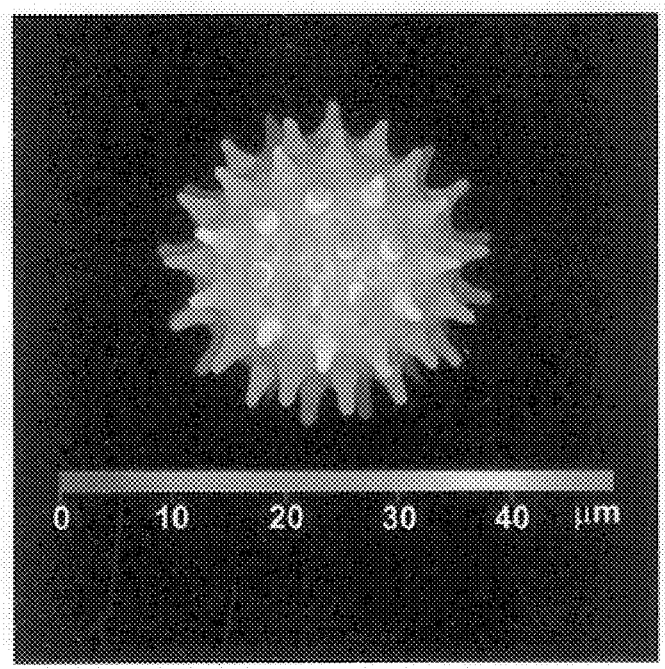
FIG. 6 shows a three-dimensional reconstruction of the pollen grain about 100 $\mu$m in diameter. The distance from each structure to the surface is indicated by color gradients.

This method can be also applied for viewing single cells labeled with non-fluorescence dyes with conventional microscope. It is also effective for tissues with autofluorescence such as Drosophila mutants expressing green fluorescence proteins or plant tissues. FIG. 6 shows a three-dimensional reconstruction of an autofluorescent pollen grain about 100 $\mu$m in diameter. The surface morphology with depth code is rendered from a stack of confocal optical sections at 5-micrometer intervals.

Although the present invention has been described with reference to the preferred embodiments thereof, it will be understood that the invention is not limited to the details thereof. Various substitutions and modifications have been suggested in the foregoing description, and others will occur to those of ordinary skill in the art. Therefore, all such substitutions and modifications are intended to be embraced within the scope of the invention as defined in the appended claims.

I claim:

1. A transparency enhancing system comprising:

an excised biological tissue; and an aqueous clearing solution selected from the group consisting of dimethyl sulfoxide, diatrizoate acid, ethylenediaminetetraacetic acid, glucamine, β-nicotinamide adenine dinucleotide phosphate, sodium diatrizoate, derivatives of polyoxyalkalene, and combinations thereof, said excised biological tissue being immersed into said aqueous clearing solution for making said biological tissue transparent for imaging.

2. The transparency enhancing system as recited in claim 1 wherein said biological tissue comprises animal cells.

3. The transparency enhancing system as recited in claim 1 wherein said biological tissue comprises plant cells.

4. The transparency enhancing system as recited in claim 1 wherein said biological tissue comprises biological organisms.

5. The transparency enhancing system as recited in claim 1 wherein said biological tissue comprises biological compounds.

6. The transparency enhancing system as recited in claim 1 wherein said aqueous clearing solution has a pH between 5 and 10.

7. The transparency enhancing system as recited in claim 1 wherein proportions of sodium diatrizoate and diatrizoate acid are greater than proportions of other components in said aqueous clearing solution.

8. The transparency enhancing system as recited in claim 1 wherein proportions of dimethyl sulfoxide are greater than proportions of other components of said aqueous clearing solution.

* * * * *